United States Patent [19]
Keller

[11] Patent Number: 5,413,608
[45] Date of Patent: May 9, 1995

[54] KNEE JOINT ENDOPROSTHESIS FOR REPLACING THE ARTICULAR SURFACES OF THE TIBIA

[75] Inventor: Arnold Keller, Kayhude, Germany

[73] Assignee: Waldemar Link GmbH & Co., Hamburg, Germany

[21] Appl. No.: 123,438

[22] Filed: Sep. 17, 1993

[30] Foreign Application Priority Data

Sep. 24, 1992 [DE] Germany .................... 9212879 U

[51] Int. Cl.$^6$ .............................................. A61F 2/38
[52] U.S. Cl. ................................................ 623/20
[58] Field of Search ............................ 623/16, 18, 20

[56] References Cited

U.S. PATENT DOCUMENTS

| 4,112,522 | 9/1978 | Dadurian et al. | 623/20 |
| 5,330,535 | 7/1994 | Moser et al. | 623/20 |

FOREIGN PATENT DOCUMENTS

| 2810748 | 11/1978 | Germany | 623/20 |

*Primary Examiner*—David Isabella
*Attorney, Agent, or Firm*—Chilton, Alix & Van Kirk

[57] ABSTRACT

Knee joint endoprosthesis for replacing the articular surfaces of the tibia, the endoprosthesis comprising a bearing part (1), which is to be anchored on the bone and has an upper bearing surface (2), and a plateau (3) which is to be secured on the said bearing part. The plateau is rotatable on the bearing surface (2) about a journal (6, 15) which co-operates with a bore (12) in the plateau (3). The bore has a flange (13) which co-operates with a removable collar (14) limiting the journal at the top. The journal is composed of a projection on the bearing part (1) and a securing part arranged on the collar (14), which can be joined together by means of one of these two parts as outer part (15) containing a bore into which the other part as inner part (6) can be inserted. In order to secure these two parts on one another, fixing means (9) are provided which can be formed by a screw arranged transversely in the journal.

9 Claims, 2 Drawing Sheets

KNEE JOINT ENDOPROSTHESIS FOR REPLACING THE ARTICULAR SURFACES OF THE TIBIA

The invention relates to a knee joint endoprosthesis for replacing the articular surfaces of the tibia, the endoprosthesis comprising a bearing part, which is to be anchored on the bone and has an upper bearing surface, and a plateau which is to be secured on the said bearing part and forms the articular surfaces to be replaced. It is known to make this plateau rotatable on the bearing surface of the bearing part about the vertical axis of the articulation so that it can yield to the rotational movements arising upon flexion of the knee. In a known prosthesis (U.S. Pat. No. 42 19 893) the centric positioning of the plateau with respect to the bearing part is secured by means of a downwardly projecting, central journal which is arranged on the plateau and penetrates into a corresponding bore in the bearing part. This has the disadvantage that the lateral guide forces on the plateau act in a plane which is offset substantially relative to the articular surfaces plane. In addition, the guide journal provided on the plateau must be designed with considerable strength, taking into consideration the limited stability of the plateau which generally consists of plastic, and this makes it necessary to provide on the bearing part for the purpose of forming the bore for the journal, a correspondingly largely dimensioned hole journal which must additionally lie coaxial to the center of rotation, which may likewise be undesirable. A further disadvantage of the known construction lies in the fact that, taking into consideration the risk of luxation, the plateau journal must be designed to be fairly long, which requires a considerable spacing of the plateau above the bearing surface of the bearing part upon insertion, which spacing is however not available if the ligaments of the knee are to be retained substantially intact. Finally, with such a design it is only with difficulty that a means of safeguarding against luxation can be provided.

According to another known prosthesis design (EP-A 186 471) a journal is provided which rises from the tibial bearing part and engages in a bore in the plateau. In terms of the spacing of the plateau above the bearing surface as required during surgery, this has the same disadvantage as the prosthesis described above. This is true to an even greater extent of those prostheses in which, after insertion of the plateau, the latter is connected to the bearing part by means of a pin (WO 92/08424, EP-A 472 475, FR-A 2 663 536). In one case (U.S. Pat. No. 4 822 366) a stud is used for this purpose, which stud passes through a bore in the plateau, has a thickened head above the plateau and is secured on the tibial bearing part with a thread provided at its lower end, a stop element fixing its screw-in position. Indications of how the prosthesis can be implanted with the ligaments intact, and without substantial longitudinal spacing of the knee joint parts, cannot be inferred from these known prostheses.

The disadvantages of the known prostheses are avoided according to the invention by virtue of the fact that the journal providing the plateau with lateral support rises from the bearing surface of the bearing part and co-operates with a bore in the plateau, the bore having a flange which safeguards against luxation and co-operates with a removable collar limiting the Journal at the top.

The construction according to the invention has the advantage of great simplicity. The lateral guide forces act on the plateau approximately in the same plane in which the articular surfaces also lie. For this reason, and because a means of safeguarding against luxation is provided, the journal can be kept very low, so that the plateau can be pushed in easily between the bearing part and the femoral condyles, with the ligaments being retained, until it lies around the journal. Since the journal arrangement is low, there is easily space for it in the saddle-shaped intercondylar area of the plateau, and it is not restricted in diameter.

The securing of the collar on the journal is expediently achieved by means of the collar being arranged on a securing part which can be joined together with a projection of the bearing part by means of one of these two parts as outer part containing a bore, into which the other part as inner part can be inserted, a fixing means being provided which acts between these two parts. The outer part is preferably arranged on the collar; however, the arrangement can also be reversed.

According to a further feature of the invention, a pin is provided for fixing purposes, this pin being held in the inner part and projecting radially out of this part in its fixing position so as to project into a recess in the outer part. This design has the advantage that the pin is secured in its position by the outer part and cannot therefore work its way out in the course of time. This is true in particular when the pin is a screw. In this case the outer part should contain a bore for receiving a screw neck, the diameter of which is smaller than that of a part of the screw adjoining the neck, so that the screw cannot pass completely outwards.

If the outer part is arranged on the collar, according to the invention the length of the screw can be greater than the diameter of the inner part, and the outer part should have an axis-parallel groove for receiving the part of the screw projecting beyond the circumference of the inner part. The screw end and the groove then act together to an angle-positioning effect in such a way as to ensure that the tool aperture provided on the outer part is situated exactly at the position at which the screw head is to be expected.

The invention is discussed in greater detail hereinbelow with reference to the drawing, which illustrates an advantageous exemplary embodiment and in which.

Figure 1:
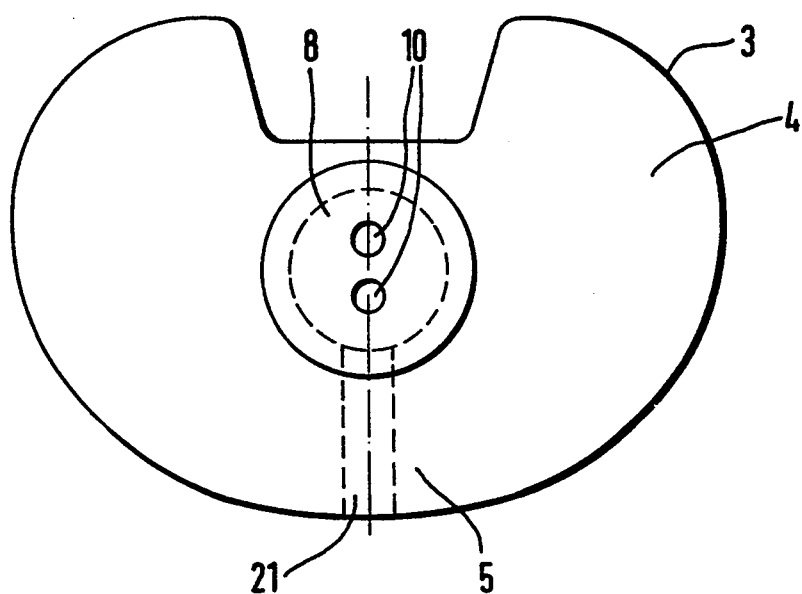
FIG. 1 shows a plan view.
Figure 2:
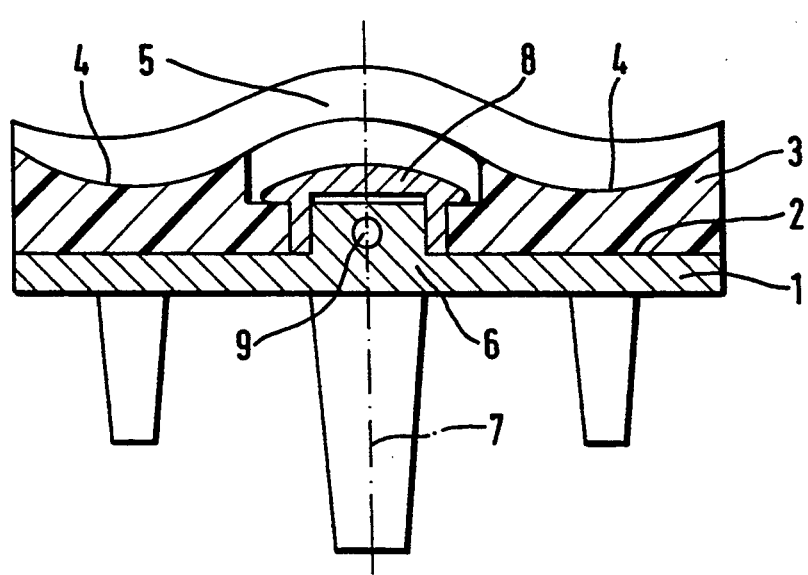
FIG. 2 shows a vertical cross-section.

The implant consists essentially of the bearing part 1, with the upper, flat bearing surface 2, and the plateau 3 whose flat lower surface lies on the bearing surface 2. The bearing part 1 consists of metal, the plateau 3 of polyethylene.

The plateau forms articular surfaces 4 between which a saddle-shaped area 5 rises. The journal arrangement is accommodated in this saddle-shaped area. This arrangement consists of the inner part 6 which is connected in one piece to the bearing part 1 and is cylindrical about the vertical axis 7, and a cap 8 which is to be attached thereon and secured by means of a screw 9. It contains in the cap two holes 10 for the engagement of the fingers of an insertion tool.

The cap 8 has a cylindrical peripheral surface 11, which is suitably comprised of a bore 12 in a flange 13 of the plateau 3. The cylindrical surface 11 ends at the top under a collar 14 whose lower surface sits over the flange 13. It forms with the bore 12 the rotational guide for the plateau 3. The collar 14 and the flange 13 together form the means of safeguarding against luxation of the plateau.

The cylindrical surface 11 is formed by a hollow cylindrical section of the cap 8. This sits suitably on the projection 6 of the bearing part 1. These parts form those elements which are referred to hereinabove and in the claims as inner part and outer part.

Figure 4:
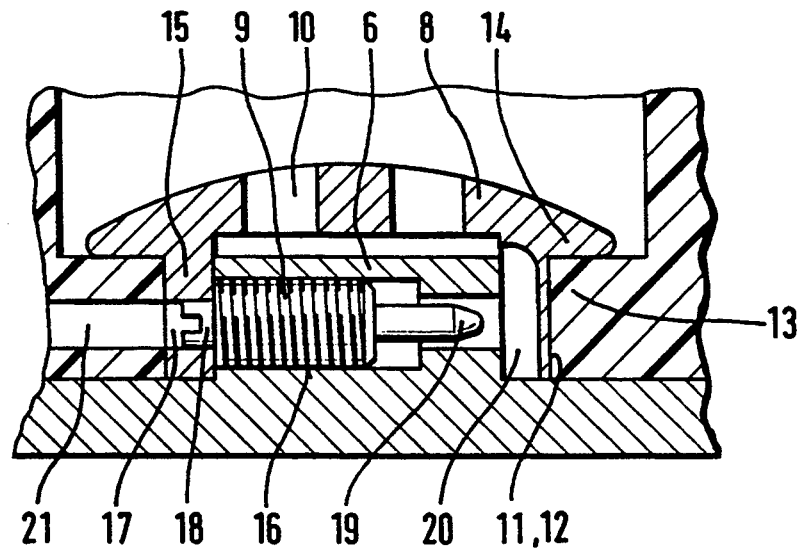

The inner part 6 contains a diametral threaded bore 16 for receiving the screw 9. At a corresponding position the outer part 15 has a bore 17 for receiving the head 18 of the screw 9. When the screw 9 is located in the end position illustrated in FIG. 4, in which the head 18 penetrates into the bore 17, the arrangement is secured in its functional position. To ensure that the screw can be brought into this position upon assembly and can be removed from this position upon disassembly, the plateau 3 has a bore 21 which is flush with the bore 17 and through which a screwdriver tool can be brought into engagement with, for example, a screw slot in the head 18 of the screw 9.

Figure 3:
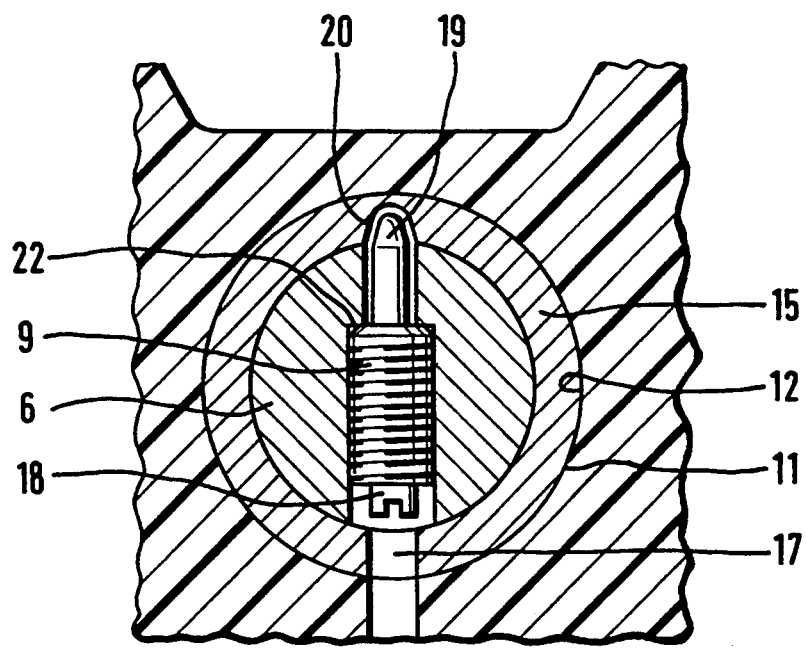
FIGS. 3 and 4 show a horizontal section and a vertical section through the journal arrangement on an enlarged scale.

The other end position of the screw, in which the cap 8 can be assembled and disassembled, is illustrated in FIG. 3. In this position the tip 19 of the screw 9 projects beyond the circumference of the inner part 6. It there acts together with an axial groove 20 in the outer part 15. The length of the screw 9 is greater than the diameter of the inner part 6. It follows from this that either the head 18 or the tip 19 of the screw projects at all times beyond the circumference of the inner part 6.

The co-operation between the tip 19 and the groove 20 facilitates assembly because this ensures that the bore 17 of the outer part 15 is flush with the screw 9 and that therefore, when slackening the screw back, the head 18 can pass safely into the bore 17. If the screw is slackened back so far that the thickened part adjoining the screw head 18, which in the case illustrated is formed by the thread, bears on the edge of the bore 17, the physician senses a corresponding resistance and can then be certain that the desired fixing position has been reached.

On the other hand, the part 8 cannot be fitted on the inner part 6 without the screw head 18 lying inside the inner part 6; then, by virtue of the length of the screw, it is guaranteed that its tip 19 protrudes from the inner part and can co-operate in a guiding function with the groove 20. In addition, provision can be made for the screw 9 and the bore 16 receiving it to be provided with a co-operating stop element 22, which ensures that the tip 19 can project from the inner part 6 no further than shown, since otherwise the attention of the operating surgeon is taken up by the question of whether the screw position is correct for assembly.

After insertion of the bearing part 1, the plateau 3 can thus be pushed over the bearing part. The cap 8 is then inserted, the nose 19 and the groove 20 providing for the correct position. A screwdriver is subsequently introduced through the bores 21 and 17, and the screw is driven in as far as the stop element into the securing position.

I claim:

1. Knee joint endoprosthesis for replacing the articular surfaces of the tibia, the endoprosthesis comprising a bearing part (1), which is to be anchored on the bone and has an upper bearing surface (2), a plateau (3) which is to be secured on the said bearing part and is rotatable on the bearing surface (2) and a journal about which the plateau rotates, characterized in that the journal (6, 15) projects from the bearing surface (2), the plateau (3) is provided with a bore cooperatively receiving the journal, the bore having a flange (13), a removable collar configured to engage the journal cooperates with the flange to limit movement of the plateau, the collar (14) has a mounting member which mates with the journal, and a fixing means (9) is provided to releasably secure the collar mounting member and journal together.

2. Knee joint endoprosthesis according to claim 1, characterized in that the fixing means includes a fastener held in the journal and the mounting member has a recess, a portion of the fastener projecting, in its fixing position, from the journal into the recess in the mounting member.

3. Knee joint endoprosthesis according to claim 1, characterized in that the fixing means includes a screw having a neck portion (9) and the mounting member contains a bore (17) for receiving the screw neck portion (18) whose diameter is smaller than that of a part of the screw adjoining the neck portion (18).

4. Knee joint endoprosthesis according to claim 1, characterized in that the fixing means is mounted on the journal and has a part (19) projecting beyond the journal, and the mounting member is a sleeve having a groove (20) extending parallel to the axis of the journal for receiving the part (19) of the fixing means projecting beyond the journal.

5. Knee joint endoprosthesis according to claim 1, characterized in that the fixing means is an elongated member and the length of the fixing means is greater than the transverse dimension of the journal.

6. Knee joint endoprosthesis according to claim 1, characterized in that the journal has a bore for receiving the fixing means, said bore having a stop element (22) for limiting movement of the fixing means along said bore.

7. Knee joint endoprosthesis according to claim 1, characterized in that one of the journal and the mounting member has an exterior surface that mates with an interior surface of the other of the journal and the mounting member.

8. Knee joint endoprosthesis according to claim 7, characterized in that the exterior surface has an aperture therein, the interior surface includes a recess, and the fixing means extends between the aperture and the recess.

9. Knee joint endoprosthesis according to claim 7, characterized in that the interior surface is on a sleeve of one of the journal and the mounting member.

* * * * *